(12) United States Patent
Oshita et al.

(10) Patent No.: US 11,713,899 B2
(45) Date of Patent: Aug. 1, 2023

(54) MANAGEMENT APPARATUS, AIR CONDITIONING MANAGEMENT SYSTEM, AND AIR CONDITIONING MANAGEMENT METHOD

(71) Applicant: Taiyo Yuden Co., Ltd., Tokyo (JP)

(72) Inventors: Junji Oshita, Tokyo (JP); Masashi Hattori, Tokyo (JP)

(73) Assignee: Taiyo Yuden Co., Ltd., Tokyo (JP)

( * ) Notice: Subject to any disclaimer, the term of this patent is extended or adjusted under 35 U.S.C. 154(b) by 232 days.

(21) Appl. No.: 16/482,165

(22) PCT Filed: Mar. 9, 2018

(86) PCT No.: PCT/JP2018/009142
§ 371 (c)(1),
(2) Date: Jul. 30, 2019

(87) PCT Pub. No.: WO2018/168672
PCT Pub. Date: Sep. 20, 2018

(65) Prior Publication Data
US 2020/0240669 A1     Jul. 30, 2020

(30) Foreign Application Priority Data
Mar. 15, 2017  (JP) ................................ 2017-049371

(51) Int. Cl.
*F24F 11/64*   (2018.01)
*F24F 11/70*   (2018.01)
(Continued)

(52) U.S. Cl.
CPC .............. *F24F 11/70* (2018.01); *F24F 11/64* (2018.01); *F24F 2110/10* (2018.01); *F24F 2110/20* (2018.01); *F24F 2110/60* (2018.01)

(58) Field of Classification Search
CPC .... F24F 11/64; F24F 2110/20; F24F 2110/10; F24F 2110/60
See application file for complete search history.

(56) References Cited

U.S. PATENT DOCUMENTS 5,261,596 A      11/1993  Tachibana et al.
2011/0172931 A1*  7/2011  Murthy ................. G16C 20/20
                                                   702/32
(Continued)

FOREIGN PATENT DOCUMENTS

CN       102866684 A      1/2013
CN       103940956 A      7/2014
(Continued)

OTHER PUBLICATIONS

Notification of Transmittal of Copies of Translation of the International Preliminary Report on Patentability dated Sep. 26, 2019 in International Application No. PCT/JP2018/009142.
(Continued)

*Primary Examiner* — Nael N Babaa
(74) *Attorney, Agent, or Firm* — Saliwanchik, Lloyd & Eisenschenk

(57) ABSTRACT

[Object] To provide a management apparatus and an air conditioning management system by which the objectivity of a comfort level evaluation relating to a smell in a room can be enhanced and a comfort level can be evaluated also with respect to an unknown smell.
[Solving Means] A management apparatus according to an embodiment of the present invention includes a detecting unit, an input unit, a storage unit, and a control unit. The detecting unit detects a smell in a room. The input unit is operated by a user who enters the room and acquires a sensory evaluation of each user which relates to the smell in the room when the user enters the room. The storage unit accumulates evaluation data obtained by associating an
(Continued)

output of the detecting unit and an output of the input unit with each other and stores a plurality of attributes relating to a comfort level of the smell in the room, the attributes being classified on the basis of the evaluation data. The control unit determines which of the plurality of attributes the output of the detecting unit belongs to.

8 Claims, 4 Drawing Sheets

(51) Int. Cl.
  *F24F 110/20* (2018.01)
  *F24F 110/10* (2018.01)
  *F24F 110/60* (2018.01)

(56) References Cited

U.S. PATENT DOCUMENTS

| | | | |
|---|---|---|---|
| 2014/0216259 A1* | 8/2014 | Iwaki | F24F 11/30 96/19 |
| 2016/0169851 A1 | 6/2016 | Lee et al. | |
| 2016/0238579 A1 | 8/2016 | Cai et al. | |
| 2017/0316995 A1* | 11/2017 | Hwang | G01N 27/123 |
| 2017/0328595 A1* | 11/2017 | Iwasaki | F24F 11/46 |

FOREIGN PATENT DOCUMENTS

| | | |
|---|---|---|
| CN | 105102899 A | 11/2015 |
| CN | 105699594 A | 6/2016 |
| CN | 105841735 A | 8/2016 |
| EP | 2 985 540 A1 | 2/2016 |
| JP | 5-10904 A | 1/1993 |
| JP | 5-44973 A | 2/1993 |
| JP | 9-66218 A | 3/1997 |
| JP | 2001-305088 A | 10/2001 |
| JP | 2007-248352 A | 9/2007 |
| JP | 2009-36492 A | 2/2009 |
| WO | WO-2016/088353 A1 | 6/2016 |

OTHER PUBLICATIONS

International Preliminary Report on Patentability dated Sep. 17, 2019 in International Application No. PCT/JP2018/009142.
International Search Report dated May 29, 2018 in International Application No. PCT/JP2018/009142.
Office Action dated Sep. 3, 2021 in Japanese Application No. 2020-149576.
Office Action dated Feb. 8, 2022 in Japanese Application No. 2020-149576.
Office Action dated Jan. 7, 2022 in Chinese Application No. 201880017915.X.
Office Action dated Jun. 18, 2021 in Chinese Application No. 201880017915.X, along with its English translation.

* cited by examiner

MANAGEMENT APPARATUS, AIR CONDITIONING MANAGEMENT SYSTEM, AND AIR CONDITIONING MANAGEMENT METHOD

CROSS-REFERENCE TO RELATED APPLICATIONS

This application is the U.S. national stage application of International Patent Application No. PCT/JP2018/009142, filed Mar. 9, 2018, which claims the benefit under 35 U.S.C. § 119 of Japan Patent Application No. 2017-049371, filed Mar. 15, 2017, which are hereby incorporated by reference in their entirety.

TECHNICAL FIELD

The present invention relates to a management apparatus and an air conditioning management system to be used for air conditioning management in a room.

BACKGROUND ART

For example, when a person enters a place where many people gather, such as a conference room and a meeting place, the person immediately senses an uncomfortable smell in some cases. In recent years, it is desirable to enhance a comfort level in an indoor environment such as a work place and a public facility. Such an enhancement can include remediation of an uncomfortable smell in a room, for example.

Regarding a smell, sensing by person is important. However, how to sense a smell depends on various factors such as a constitution, a condition, a temperature, and a humidity. The following phenomena have been empirically well known. Specifically, as one of the phenomena, when a person keeps sensing the same smell, the person cannot know anymore what is that smell. As another one of the phenomena, a person cannot realize changes in smell which is changing little by little.

In view of this, various methods for expressing smell comfort as numerical values have been proposed in recent years. For example, Patent Literature 1 has described as follows. A correspondence relationship between characteristic values calculated on the basis of an output of a semiconductor gas sensor with respect to various types of odor gas and odor-sensing data in two-dimensional coordinates defined by a coordinate system representing comfortable and uncomfortable levels and a coordinate system representing excitation and sedation levels in human electroencephalographic data with respect to various types of odor gas is generated in advance. By using it, a sense when a parson senses gas which is a target to be measured is associated with it.

CITATION LIST

Patent Literature

Patent Literature 1: Japanese Patent Application Laid-open No. 2007-248352

DISCLOSURE OF INVENTION

Technical Problem

However, a simply high uncomfortable index does not necessarily indicate a smell that all people feel uncomfortable. Therefore, the objectivity of a comfort level evaluation is insufficient. Further, it is impossible to express all smells as numerical values. Therefore, it is difficult to perform comfort determination with respect to an unknown smell.

In view of the above-mentioned circumstances, it is an object of the present invention to provide a management apparatus and an air conditioning management system by which the objectivity of a comfort level evaluation relating to a smell in a room can be enhanced and a comfort level can be evaluated also with respect to an unknown smell.

Solution to Problem

In order to accomplish the above-mentioned object, a management apparatus according to an embodiment of the present invention includes a detecting unit, an input unit, a storage unit, and a control unit. The detecting unit detects a smell in a room. The input unit is operated by a user who enters the room and acquires a sensory evaluation of each user which relates to the smell in the room when the user enters the room. The storage unit accumulates evaluation data obtained by associating an output of the detecting unit and an output based on the sensory evaluation of the input unit with each other and stores a plurality of attributes relating to a comfort level of the smell in the room, the attributes being classified on the basis of the evaluation data.

The control unit determines which of the plurality of attributes the output of the detecting unit belongs to.

The management apparatus is configured to determine a comfort level of a current smell on the basis of detection data relating to the smell in the room which is acquired via the detecting unit and the sensory evaluation of each user which relates to the smell when the user enters the room and is acquired via the input unit. With this configuration, the objectivity of a comfort level evaluation relating to a smell in a room can be enhanced and a comfort level can be evaluated also with respect to an unknown smell.

The input unit may be configured to acquire one sensory evaluation selected by each user from among a plurality of sensory evaluations relating to the smell in the room. With this configuration, variations in the smell evaluation can be reduced and more objective evaluation results can be obtained.

The control unit may be configured to classify the plurality of attributes on the basis of evaluation data accumulated in the storage unit and update a threshold to be used for attribute determination of the output of the detecting unit. By accumulating the data for evaluation, the reliability or the objectivity can be enhanced.

The detecting unit may include a first sensor configured to be capable of detecting a plurality of types of gas. The first gas sensor may include a QCM sensor.

The detecting unit may further include a second sensor configured to be capable of detecting at least one of a temperature or a humidity in the room.

An air conditioning management system according to an embodiment of the present invention includes a detecting unit, an input unit, a storage unit, an air conditioning apparatus, and a control unit. The detecting unit detects a smell in a room. The input unit is operated by a user who enters the room and acquires a sensory evaluation of each user which relates to the smell in the room when the user enters the room. The storage unit accumulates evaluation data obtained by associating an output of the detecting unit and an output based on the sensory evaluation of the input unit with each other and stores a plurality of attributes relating to a comfort level of the smell in the room, the attributes being classified on the basis of the evaluation data. The air conditioning apparatus conditions air in the room. The control unit determines which of the plurality of attributes the output of the detecting unit belongs to and controls the air conditioning apparatus on the basis of a control indication corresponding to the determined attribute.

Advantageous Effects of Invention

As described above, in accordance with the present invention, the objectivity of a comfort level evaluation relating to a smell in a room can be enhanced and a comfort level can be evaluated also with respect to an unknown smell.

MODE(S) FOR CARRYING OUT THE INVENTION

Hereinafter, embodiments of the present invention will be described with reference to the drawings.

First Embodiment

Figure 1:
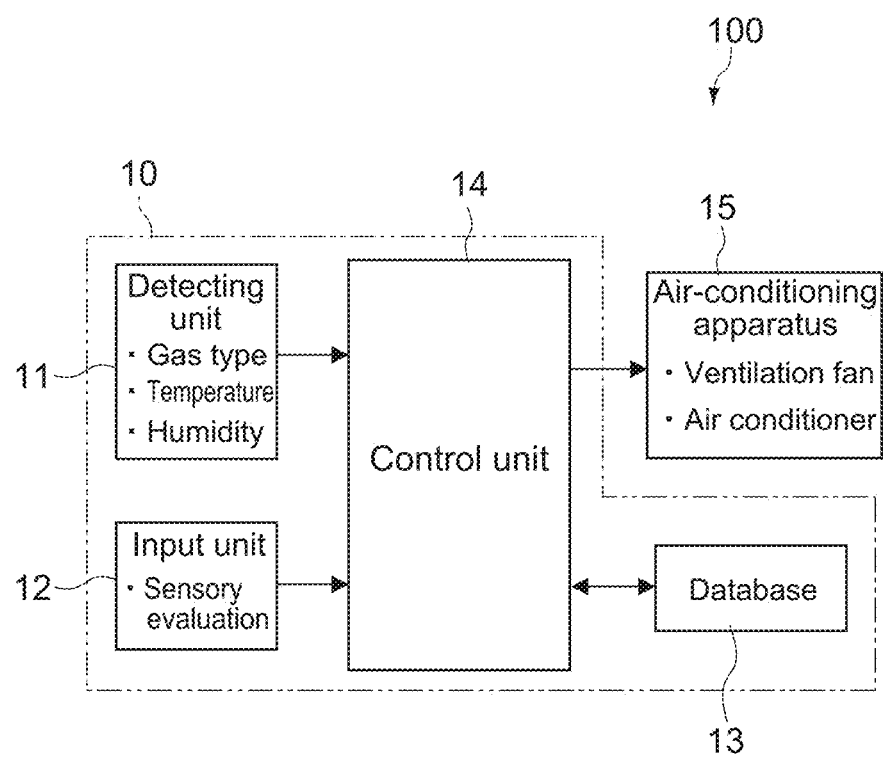
FIG. 1 A block diagram showing a configuration of an air conditioning management system including a management apparatus according to an embodiment of the present invention.

FIG. 1 is a block diagram showing a configuration of an air conditioning management system 100 including a management apparatus 10 according to an embodiment of the present invention.

The air conditioning management system 100 includes the management apparatus 10 and an air conditioning apparatus 15. The air conditioning management system 100 is configured to be capable of managing an indoor environment (in particular, a comfort level relating to a smell) such as a conference room (not shown) and controlling an operation of the air conditioning apparatus 15 such as an air conditioner (hereinafter, referred to as AC) and a ventilation fan on the basis of a sensory evaluation by a user who utilizes that conference room typically including a person present in a room, a person who enters the room, and the like. Hereinafter, a space which is a target to be managed, such as an inside of a conference room, will be referred to as "in the room".

[Management Apparatus] The management apparatus 10 includes a detecting unit 11, an input unit 12, a database 13 (storage unit), and a control unit 14.

(Detecting Unit) The detecting unit 11 includes a gas sensor (first sensor) that detects the smell in the room. The detecting unit 11 is configured to be capable of detecting a plurality of types of gas. With this configuration, it is possible to increase types of smell that can be detected and to detect smells of a plurality of types of mixed gas as a composite smell. The output of the detecting unit 11 is input into the control unit 14.

Gas which is a target to be detected is not particularly limited and may be a substance causing the smell or may include a substance other than the substance causing the smell. Examples of the gas which is the target to be detected can include acetone, toluene, formaldehyde, methyl ethyl ketone, methyl cyclohexane, ethanol, ammonia, and water vapor. Although the number of gas types is not particularly limited, it is favorable that the number of gas types is as large as possible. For example, three or more gas types are detected.

Although a configuration of the gas sensor is also not particularly limited, it is favorable that it is a configuration with which the type and amount (concentration) of detected gas can be expressed as numerical values. The numerical value set forth herein refers to an amount of change in output which has changed after gas is added, provided that a state in which the gas (smell molecules and the like) is absent is zero. A quartz crystal microbalance (QCM) sensor, a semiconductor sensor, or the like can be typically employed as a gas sensor therefor. One gas sensor may be used for one gas type. Alternatively, a gas sensor capable of detecting a plurality of gas types may be used.

In this embodiment, a QCM sensor is used as the gas sensor. The QCM sensor includes an oscillator and a gas absorbing film. The gas absorbing film is provided on a surface of the oscillator. The QCM sensor is configured to detect a gas type absorbed in the gas absorbing film on the basis of a change in resonant frequency of the oscillator. The gas absorbing film typically includes at least one of a water-soluble film, a hydrophobic film, or a hydrophilic film. With this configuration, various gas types (smell components) can be detected. It should be noted that a well-known QCM sensor can be used as the QCM sensor and a detailed description thereof is omitted here.

The detecting unit 11 further includes a temperature and humidity sensor (a second sensor) that detects a temperature and a humidity in the room. The detecting unit 11 may be configured to be capable of detecting a temperature and a humidity and or may be configured to be capable of detecting any one of the temperature or the humidity. With this configuration, states of various environments also including temperature data and humidity data can be expressed as numerical values.

In general, how to sense a smell is liable to be affected by environment factors such as a temperature and a humidity. In view of this, by configuring the detecting unit 11 capable of detecting not only the gas type but also the temperature and humidity at the same time, it becomes possible to determine an evaluation of the comfort level relating to the smell while considering environment factors such as the temperature and the humidity.

For example, a temperature sensor and a humidity sensor are used for detecting the temperature and the humidity. One sensor may be used to detect the temperature and the humidity at the same time. Although the type of the temperature and humidity sensor is not particularly limited, the QCM sensor may be used. For example, the temperature sensor can be configured by using a material sensitive to a temperature change as the oscillator (crystalline). The humidity sensor can be configured by using an absorbing film capable of absorbing water vapor.

(Input Unit) The input unit 12 is operated by a user who enters the room is configured to be capable of acquiring an sensory evaluation of each user relating to the smell in the room when the user enters the room.

The sensory evaluation refers to an indication of a comfort level relating to the smell in the room, which the user senses when the user enters the room. The sensory evaluation is a subjective evaluation that each user felt consequently, which includes any type of smell, for example, comfortable and uncomfortable. It is because how to sense a smell is affected also by a condition, a constitution, and the like and intrinsically depends on differences among individuals. Therefore, the sensory evaluation may be a result depending on each user.

Although a configuration of the input unit 12 is not particularly limited, mechanical or electromagnetic various input apparatuses including input keys (of press type, slide type, or touch type) can be employed. The input unit 12 is placed at an entrance (door) or on a wall surface or the like near it, for example. With this configuration, evaluations of users can be immediately collected. Therefore, the reliability of evaluations is enhanced. The output of the input unit 12 is input into the control unit 14.

Although the sensory evaluation typically involves variations between individual users, it is favorable to present a plurality of predetermined selection candidates and selectively collect sensory evaluations of the respective users. In view of this, in this embodiment, the input unit 12 is configured to acquire one sensory evaluation selected by each user from among the plurality of sensory evaluations relating to the smell in the room. With this configuration, variations in the smell evaluations can be reduced and more objective evaluation results can be obtained.

Figure 2:
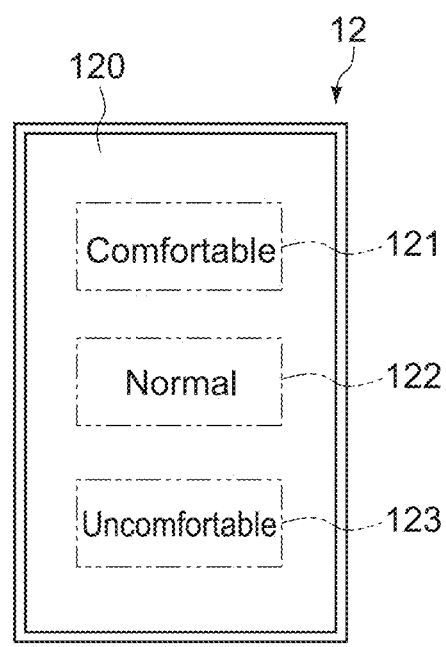
FIG. 2 A schematic front view showing a configuration example of an input unit in the management apparatus.

FIG. 2 is a schematic front view showing a configuration example of the input unit 12. The input unit 12 shown in the figure includes a touch sensor. The input unit 12 shown in the figure includes an input screen 120 capable of displaying three keys (graphic user interfaces (GUIs)) 121, 122, and 123 respectively indicating "comfortable", "normal", and "uncomfortable". The input unit 12 shown in the figure is configured such that a user who enters the room can selectively perform an input operation on any one of the keys.

(Database) The database 13 is for accumulating evaluation data obtained by associating the output of the detecting unit 11 and the output of the input unit 12 with each other.

The evaluation data refers to data in which the output of the detecting unit 11 and the output of the input unit 12 are associated with each other temporally in synchronization with each other. The evaluation data corresponds to a data set in which the sensory evaluation acquired by the input unit 12 and the output of the detecting unit 11 at that time are associated with each other, for example. The evaluation data is generated at the control unit 14 and is stored in the database 13 via the control unit 14. Further, the evaluation data is generated every time the user enters the conference room and is accumulated in the database 13.

The database 13 is further configured to be capable of storing attributes (comfortable, normal, uncomfortable, and the like) relating to the comfort level relating to the smell in the room, which are classified in advance. The plurality of attributes are classified on the basis of the evaluation data by the control unit 14 as will be described later.

A configuration of the database 13 is not particularly limited. Typically, the database 13 includes a nonvolatile storage apparatus such as a semiconductor memory and a hard disk drive (HDD). The database 13 is placed not only in the room but also in other places via a wired or wireless network. Further, the database 13 may include a cloud server and the like.

(Control Unit) The control unit 14 includes a computer including a CPU and an internal memory. The control unit 14 is configured to determine which of the plurality of attributes relating to the comfort level of the smell in the room, which are classified in advance on the basis of the above-mentioned evaluation data, the output of the detecting unit 11 belongs to.

Figure 3:
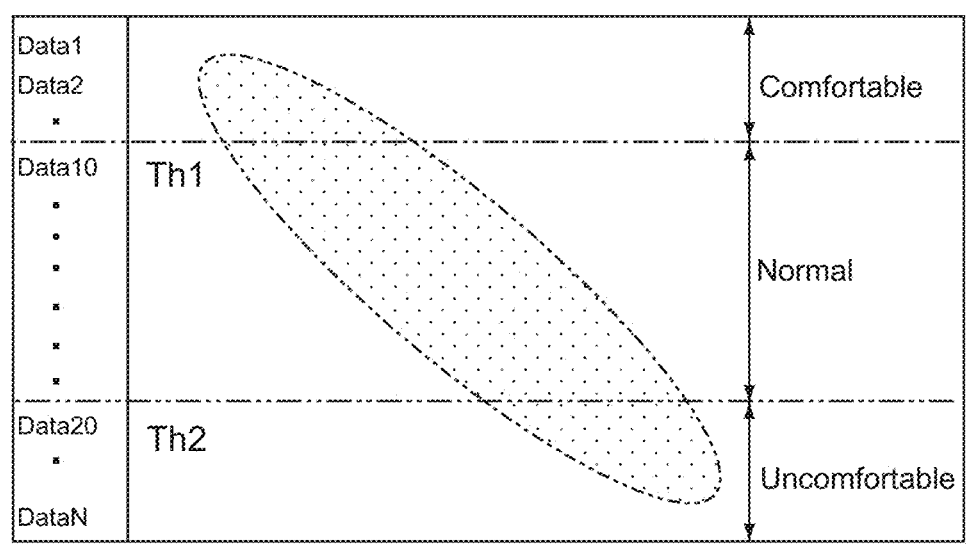
FIG. 3 A correlation diagram schematically showing a relationship between evaluation data generated at a control unit in the management apparatus and an attribute.

FIG. 3 is a correlation diagram schematically showing a relationship between the evaluation data and the attribute. Here, regarding the comfort level of the smell, three attributes of "comfortable", "normal", and "uncomfortable" are shown. Those attributes correspond to the sensory evaluations of the users, which are selectively input via the input unit 12.

As described above, the evaluation data includes the sensory evaluation of the user and the output of the detecting unit 11 at that time. Therefore, there is a certain correlation between the output of the detecting unit 11 and the "smell". In addition, the output of the detecting unit 11 includes data relating to a plurality of gas types and data relating to a temperature and a humidity. Therefore, there can be a predetermined correlation also between the output data of each type of gas and the temperature and humidity data also in the output of the detecting unit 11 which is inherent in the sensory evaluation of the user. Therefore, in this embodiment, a configuration in which outputs of the detecting unit 11 (smell data, temperature, and humidity data) are classified into attributes and a determination as to which of the plurality of classified attributes a current output of the detecting unit 11 belongs to is performed, to thereby evaluate or manage a comfort level relating a current smell in the room is employed.

Although the plurality of attributes are typically classified by the control unit 14, the original classification may be set by default or may be actual values in the past may be employed. Alternatively, as will be described later, a threshold of data used for classification may be reset (updated) on the basis of the latest evaluation data.

The attributes are typically classified performed by comparing various types of data acquired by the detecting unit 11 with a predetermined threshold. In this embodiment, the attributes are classified into three or more attributes. Therefore, at least two or more thresholds (in FIG. 3, Th1 and Th2) are set.

The threshold is determined by performing regression analysis and the like on the accumulated evaluation data. The attributes (comfortable, normal, uncomfortable) are determined on the basis of which threshold range the output of the detecting unit 11 belongs to. Reference data originally prepared may be used for the threshold or the threshold may be an actual value in the past. Alternatively, the threshold may be configured to be able to be updated by a machine learning device or a learning function using a deep learning technique.

Each threshold may be set on the basis of composite data in which the smell data is combined with the temperature and humidity data. Alternatively, each threshold may include a combination of a plurality of types of thresholds each set with only smell data or only the temperature and humidity data.

A criteria for setting those thresholds is not particularly limited. For example, it can be set to an appropriate value with which a determination result adaptive to sensory evaluations of the majority users in the room can be obtained. Further, as the number of classified attributes becomes larger, the number of thresholds al so becomes larger.

Therefore, for example, the strictness of the threshold may be enhanced as the number of attributes becomes larger.

The control unit 14 is configured to control the air conditioning apparatus 15 on the basis of a control indication corresponding to the determined attribute.

The air conditioning apparatus 15 typically includes various types of air conditioning installation such as a ventilation fan, an air cleaner, a humidifier, a dehumidifier, and an AC. Regarding the control indication, it is varied in a manner that depends on the types of air conditioning installation and includes turning on/off of operation as a matter of course, and air flow settings such as a strength, an air volume, and a wind direction, and further, changes in set values of desired controlled values of the temperature and the humidity and the like. Different types of control are executed in a manner that depends on the types of the determined attributes. For example, if it is determined that the attribute is "comfortable" or "normal", a current air conditioning setting is maintained. On the other hand, if it is determined that the attribute is "uncomfortable", various types of air conditioning installation operations are controlled such that the air conditioning setting becomes "comfortable" or "normal". In the following description, the operation of improving the indoor environment by the air conditioning apparatus 15 will be also referred to as "ventilation".

[Operation of Management Apparatus] Next, the control unit 14 will be described in detail along with a typical operation of the management apparatus 10.

Figure 4:
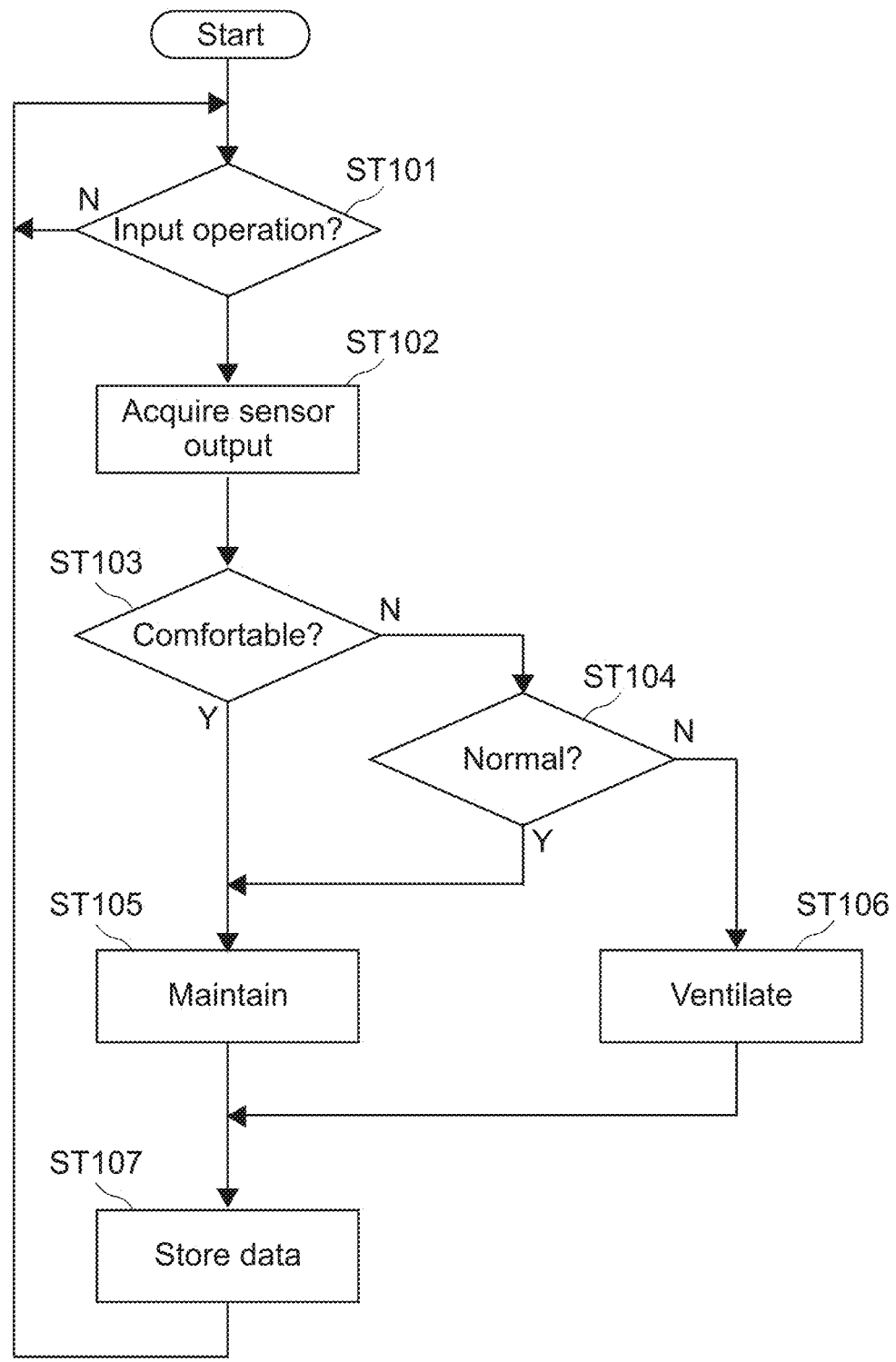
FIG. 4 A flowchart showing an example of a processing procedure of the control unit.

FIG. 4 is a flowchart showing an example of a processing procedure of the control unit 14.

The management apparatus 10 is powered on. Then, the detecting unit 11 starts to be driven. The input unit 12 shifts to a stand-by state in which it waits for an input operation. The processing of the control unit 14 is thus started. The control unit 14 detects whether or not the input operation is performed on the input unit 12. If the input operation is detected, the control unit 14 acquires the smell data in the room and the temperature and humidity data from the detecting unit 11 (Steps 101 and 102).

In this embodiment, a configuration to acquire the output of the detecting unit 11 when the input unit 12 receives the input operation is employed. Alternatively, a configuration to constantly sample outputs of the detecting unit 11 and monitor changes in indoor environment even in a period in which the input operation is not performed may be employed.

Next, the control unit 14 determines which of the plurality of attributes (comfortable, normal, uncomfortable) relating to the comfort level of the smell in the room, which are classified in advance, the output of the detecting unit 11 belongs to (Steps 103 and 104). Here, attribute data prestored in the database 13 is referred to and the attribute relating to the comfort level in the room is determined on the basis of which of regions divided with thresholds Th1 to Th2 (see FIG. 3) the output of the detecting unit 11 belongs.

As a result, if it is determined that the attribute is "comfortable" or "normal", a smell environment in the room is considered as being favorable and a current air conditioning environment is maintained (Step 105). On the other hand, if it is determined that the attribute is neither "comfortable" or "normal", it is determined that the smell environment in the room is "uncomfortable" and the room is ventilated by controlling the air conditioning apparatus 15 with a predetermined control indication in order to ventilate the indoor environment (Step 106).

Subsequently, the control unit 14 generates evaluation data in which the acquired output of the detecting unit 11 and the sensory evaluation of the input unit 12 are associated with each other and accumulates it in the database 13 (Step 107). That evaluation data is used as an evaluation sample to be referred to in the subsequent attribute determination and is added as one of elements constituting the attribute corresponding to this determination result (see FIG. 3). By accumulating the evaluation data, the reliability or the objectivity can be enhanced.

By repeatedly executing the above-mentioned operation every time the user enters the room, optimal air conditioning control adaptive to changes in smell in the room is performed.

In accordance with this embodiment, a smell evaluation criteria is dynamically changed in accordance with a sensory evaluation of each user. Therefore, the objectivity of the comfort level evaluation relating to the smell in the room is enhanced and a comfortable air conditioning environment substantially adaptive to feelings of all users can be maintained.

Further, in accordance with this embodiment, whether or not a current smell is uncomfortable is determined on the basis of only a sensory evaluation of each user without identifying a cause of the smell. Therefore, a suitable comfort level evaluation can be performed also with respect to an unknown smell.

Second Embodiment

Figure 5:
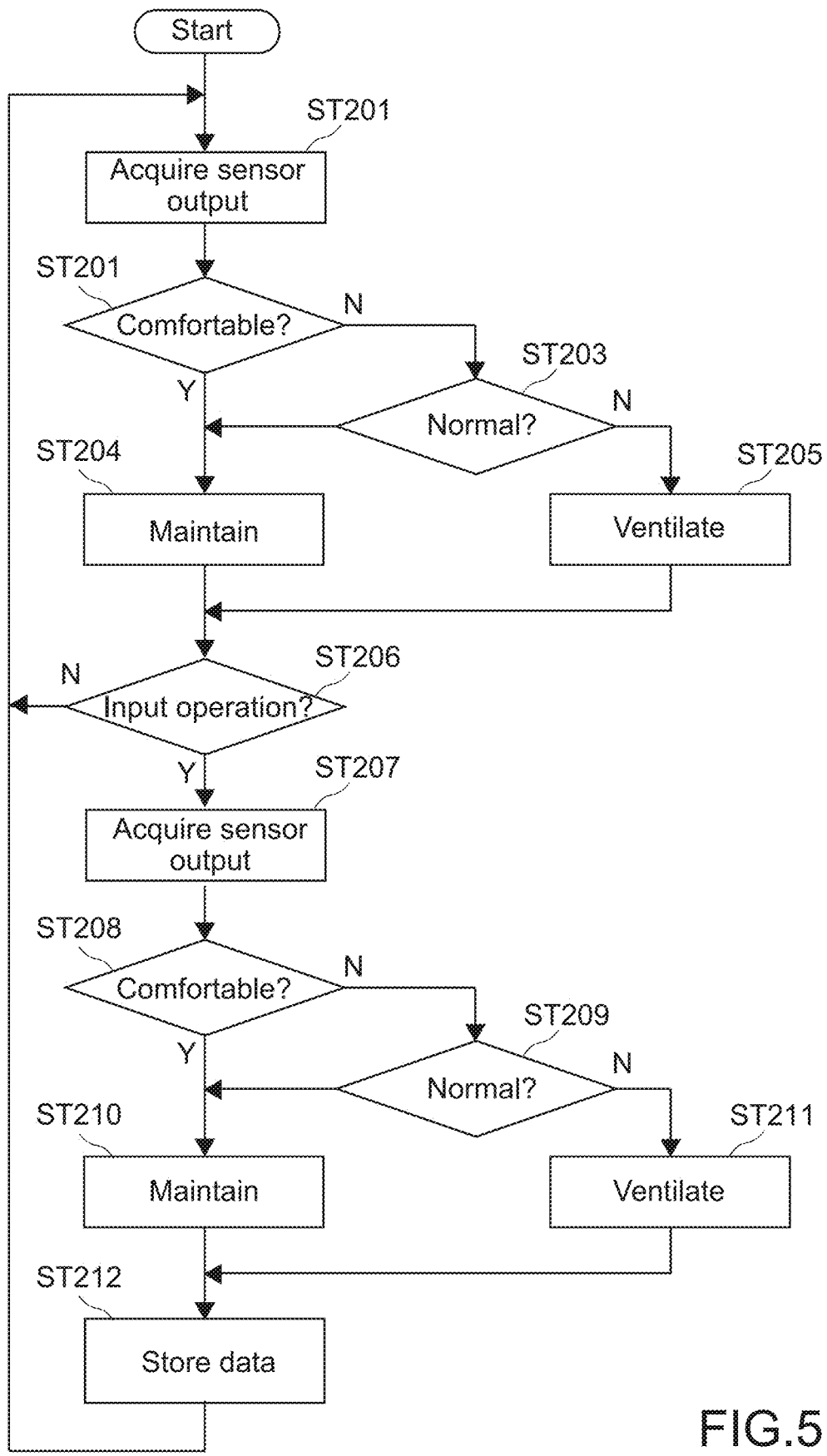
FIG. 5 A flowchart showing an example of a processing procedure of a control unit in a management apparatus according to another embodiment of the present invention.

FIG. 5 is a flowchart showing an example of a processing procedure of a control unit 14 in a management apparatus according to a second embodiment of the present invention. Hereinafter, configurations different from those of the first embodiment will be mainly described and configurations similar to those of the first embodiment will be denoted by similar signs and descriptions thereof will be omitted or simplified.

In this embodiment, a configuration to monitor the indoor environment on the basis of the output of the detecting unit 11 not only during input operation on the input unit 12 but also before the input operation on the input unit 12 is performed and to spontaneously control the air conditioning apparatus 15 and execute an operation of ventilating the room if a condition under which it is determined that the attribute is "uncomfortable" is satisfied is employed.

As shown in FIG. 5, when the management apparatus 10 is powered on, the control unit 14 acquires the output of the detecting unit 11 and executes an attribute determination as to whether or not the indoor environment relating to the current smell is uncomfortable (Steps 201 to 203). Also in this attribute determination, attribute data stored in the database 13 is referred to and the attribute is determined on the basis of which of regions divided with thresholds Th1 to Th2 (see FIG. 3) the output of the detecting unit 11 belongs.

As a result of determination, if it is determined that the attribute is "comfortable" or "normal", the smell environment in the room is considered as being favorable and the current air conditioning environment is maintained (Step 204). On the other hand, if it is determined that the attribute is neither "comfortable" or "normal", it is determined that the smell environment in the room is "uncomfortable" and an improvement of the indoor environment is achieved by controlling the air conditioning apparatus 15 with a predetermined control indication to ventilate the indoor environment (Step 205).

The above-mentioned operation is repeatedly executed until the input operation on the input unit 12 is detected.

On the other hand, if the input operation on the input unit 12 is detected, as in the first embodiment, the smell data in the room and the temperature and humidity data are acquired from the detecting unit 11 and which attribute the output of the detecting unit 11 belongs is determined (Steps 206 to 209). Then, the current air conditioning environment is maintained (Step 210) if it is determined that the attribute is "comfortable" or "normal". On the other hand, the room is ventilated by controlling the air conditioning apparatus 15 with a predetermined control indication (Step 211) if it is determined that the attribute is neither "comfortable" or "normal".

After that, as in the first embodiment, the control unit 14 generates evaluation data in which the acquired output of the detecting unit 11 and the sensory evaluation of the input unit 12 are associated with each other and accumulates it in the database 13 (Step 212). That evaluation data is used as an evaluation sample to be referred to in the subsequent attribute determination and is added as one of elements constituting the attribute corresponding to this determination result (see FIG. 3).

As described above, in accordance with this embodiment, the configuration to maintain an optimal indoor environment in accordance with an environment change also before the sensory evaluation of the user is performed is employed. Therefore, an uncomfortable smell environment when each user enters the room can be effectively inhibited. Further, even if a new smell cause occurs after that, it is possible to posteriorly achieve an improvement of the environment after the sensory evaluation of the user is performed and to efficiently utilize that smell data for the subsequent attribute determination.

Hereinabove, the embodiments of the present invention have been described and the present invention is not limited only to the above-mentioned embodiments and various modifications can be made as a matter of course.

For example, in the above-mentioned embodiments, the descriptions have been made by exemplifying management of the comfort level relating to the smell in the conference room, though not limited thereto. The present invention is applicable also to management and the like of a comfort level in a work place environment such as an office room and a factory, a public facility such as a meeting place, a vehicle inner space of public transportation such as a bus and a train.

Further, in the above-mentioned embodiments, the descriptions have been made by exemplifying the comfort level management in the single independent room. Alternatively, insides of a plurality of rooms may be managed at the same time. With this configuration, a plurality of pieces of evaluation data can be efficiently collected from smell data of the respective rooms. Therefore, it becomes easy to form a database and it is also possible to efficiently perform air conditioning management of each room.

REFERENCE SIGNS LIST 10 management apparatus
11 detector
12 input unit
13 database (storage unit)
14 control unit
15 air conditioning apparatus
100 air conditioning management system

The invention claimed is:

1. A management apparatus, comprising:
a gas sensor that detects a smell in a room;
an input apparatus that is operated by a user who enters the room and acquires a sensory evaluation of the user that relates to the smell in the room when the user enters the room;
a database that accumulates a plurality of data sets, each of the plurality of data sets including a sensory evaluation acquired by the input apparatus at a first point in time and a first output of the gas sensor at the first point in time, and stores a plurality of attributes relating to a comfort level of the smell in the room, the plurality of attributes being classified on a basis of the plurality of data sets; and
a computer that determines an attribute at a second point in time corresponding to a second output of the gas sensor at the second point in time from among the plurality of attributes based on the plurality of data sets, the second point in time being later than the first point in time.

2. The management apparatus according to claim 1, wherein
the input apparatus acquires one sensory evaluation selected by the user from among a plurality of sensory evaluations relating to the smell in the room.

3. The management apparatus according to claim 2, wherein
the computer sets a threshold based on the plurality of data sets and determines the attribute based on whether the second output of the gas sensor at the second point in time is greater than or less than the threshold.

4. The management apparatus according to claim 1, wherein the gas sensor is configured to be capable of detecting a plurality of types of gas.

5. The management apparatus according to claim 4, wherein
the first sensor includes a QCM sensor.

6. The management apparatus according to claim 4, further comprising a temperature and/or humidity sensor configured to be capable of detecting at least one of a temperature or a humidity in the room.

7. The management apparatus according to claim 1, wherein
the sensory evaluation of the user is one of the plurality of attributes selected by the user in accordance with the first output of the gas sensor.

8. The management apparatus according to claim 1, wherein
the plurality of attributes are classified on a basis of a relationship between the sensory evaluation at the first point in time and the first output of the gas sensor at the first point in time in the plurality of data sets, and
the computer determines the attribute based on the relationship between the sensory evaluation at the first point in time and the first output of the gas sensor at the first point in time in the plurality of data sets.

* * * * *